US006448082B1

(12) United States Patent
Prevots et al.

(10) Patent No.: US 6,448,082 B1
(45) Date of Patent: Sep. 10, 2002

(54) DNA SEQUENCES CONTAINING A CONJUGATIVE TRANSFER MECHANISM

(75) Inventors: Fabien Prevots, Donneville; Marlène Daloyau, Montgiscard, both of (FR)

(73) Assignee: SKW Biosystems, Boulogne-Billancourt (FR)

( * ) Notice: Subject to any disclaimer, the term of this patent is extended or adjusted under 35 U.S.C. 154(b) by 0 days.

(21) Appl. No.: 09/623,062

(22) PCT Filed: Dec. 28, 1999

(86) PCT No.: PCT/FR99/03297

§ 371 (c)(1),
(2), (4) Date: Aug. 25, 2000

(87) PCT Pub. No.: WO00/39312

PCT Pub. Date: Jul. 6, 2000

(30) Foreign Application Priority Data

Dec. 29, 1998 (FR) ............................................. 98 16529

(51) Int. Cl.⁷ ............................ C12N 15/03; C12N 1/21; C12N 15/63; C12N 15/74; C07H 21/04

(52) U.S. Cl. .................... 435/454; 435/243; 435/252.3; 435/320.1; 435/471; 536/24.1

(58) Field of Search ..................... 536/24.1; 435/243, 435/252.3, 320.1, 471, 454

(56) References Cited

PUBLICATIONS

Fitzgerald et al, Applied and Environmental Microbiology, Sep. 1996, vol. 62, No. 9, pp. 3075–3082.*

* cited by examiner

Primary Examiner—Terry McKelvey
(74) Attorney, Agent, or Firm—Antonelli, Terry, Stout & Kraus, LLP

(57) ABSTRACT

The invention relates to a DNA sequence capable of being transferred by conjugation, which comprises the sequence SEQ ID No: 2. The invention further relates to the use of this DNA sequence and to a method of carrying it out.

46 Claims, 2 Drawing Sheets

SEQUENCE LISTING

<160> NUMBER OF SEQ ID NOS: 23

<210> SEQ ID NO 1
<211> LENGTH: 5333
<212> TYPE: DNA
<213> ORGANISM: Lactococcus lactis

<400> SEQUENCE: 1
gaattcaaaa atataatgct tattttagta ttagtaacca tctctataat tttaaatata      60
ttaattaacc gatttattat ttttcatcac ttagggataa tgaataatca aattaatatt     120
gatagtatat taagttcttt atcatgttta ggaaaaattt ttggtattgc cttattagcc     180

-continued

| | | | | | |
|---|---|---|---|---|---|
| cccatactcg | aagaaagtat | tttcagagcg | tctatttacc | aaatcttcat | taatgataaa | 240 |
| gtttcttttc | ttatctctag | cttactattt | gcattttttac | ataggggtta | tagttgggtt | 300 |
| ttcttcacgt | atctgccagt | aagtttatgt | atgacattta | tctatcatcg | cagaaaaata | 360 |
| ttgacagatt | ccattctatt | tcattcgtta | tttaatttat | tagtattggg | tttgaatttt | 420 |
| ttaatatgaa | ataaatttta | gaatagtact | tacttttttgg | ataaatagta | aaattataga | 480 |
| aacgattcat | tattggttct | cagatgtcta | tagagttgga | cactttcagt | gtttagataa | 540 |
| aaattaggac | taacaagtaa | ctactgaaat | attaaccaat | tatagtttat | aaaaaaacga | 600 |
| aggataaata | tacatgctag | acattttaaa | taaagcaaga | atacataaaa | aatggttcct | 660 |
| atttttcatat | tcaattatct | ctttttttgtat | tacaattatt | tatattgttt | ttaatcacac | 720 |
| atttttttaaa | gttaattggg | caaaatataa | tagcgatgac | agctataaaa | ataaagtaga | 780 |
| tgagatttta | aagcatggag | ttttctggat | taatggaaat | ttaacatcta | ttagttcgcc | 840 |
| attattaatt | tgccttttct | tgcttggtgc | attcttttca | ttaactattt | tcttcttaac | 900 |
| ttggagaaat | ttatcgacta | gaacatggac | cccaattata | tcctttcttg | gatttctgat | 960 |
| tccatttatt | catagtgatg | gaaatttcat | aaatttattg | atttttatctt | ttattcttat | 1020 |
| actatttggg | gctatttcct | ctgttcctag | tcttagatat | ttttaaatat | tacagcccaa | 1080 |
| aatgaatact | taaaaatatc | attcactctt | tatatgctaa | tacccttaag | aagtctcaaa | 1140 |
| tacgaacgaa | aaatattcta | atagggtcat | ctatcacata | aatctactct | atgctaaaaa | 1200 |
| caaaaatctt | atttaataat | tatattctca | tttctatctg | tagtgtttat | taatatttttt | 1260 |
| gaaagataaa | gatagaaaga | attaatcatt | aaactatcag | aaattacaaa | aatggctagc | 1320 |
| atactgctta | gccattttta | ttttaattct | gcgaaccgag | ggggttaagg | gtggagcttt | 1380 |
| gctccccctt | acaagcgcca | caatagccac | gaagtggcta | gcttgtgggt | tgcttgccaa | 1440 |
| gactttatct | ttattctagc | ttttgagggt | cgagcttgag | cgtcggacac | gaaaagtgct | 1500 |
| agaataaaga | tatggacgga | acgtccatgg | aaaggcgggg | gttatgagcg | aacacttaaa | 1560 |
| tatggctagc | attaaaaaga | aacaaccaaa | tcgaaaagaa | cgaaaacaaa | taagtttcag | 1620 |
| agtgagcgaa | ccggaatatt | taaaccttga | gcgctcagcg | aaagtcttaa | atatttcggt | 1680 |
| gccggctttt | gtcaaaaaga | aggcacaagg | cgctcgtgtc | gtcgcaccta | aaattaatcc | 1740 |
| agacgattca | aaagaaatgg | ctcgccagtt | ggcagcactt | ggcaataacg | tgaatcaact | 1800 |
| cgctaaaagg | gtcaatcaga | ttgaatttgc | ggataaggac | acgcaagagc | gcctatcagc | 1860 |
| cgatttaagg | cgcaccttac | acggtctggg | ggaaatatgg | cgacaactca | cataaaacgc | 1920 |
| tcaaatggcg | cttctagact | cgtcaactac | gctgaaaaaa | gagcggttca | aaagacggc | 1980 |
| tataatttag | acattgagta | tgccaaatct | gaactcaaac | aagttcgaga | aatttacgga | 2040 |
| aacaaagggg | caacgcaagc | ctacgcttca | agagtggcat | tctctccgaa | agaatttgac | 2100 |
| cctaaaaatg | taaaagacca | actaaaggca | ctagaaatcg | ctaaagaaat | ctattcaacc | 2160 |
| gcctatccca | accaacaaat | cgcaatgtat | gttcacaacg | acaccgattc | cctccacgtt | 2220 |
| cacgccgtga | ttggcgccat | taacctacta | acaggtaaaa | aaatgcacgg | caattggcaa | 2280 |
| gaataccgtg | aaaggctcgt | taaaataacg | gataaagtcg | tggagaaaca | tggcttaacc | 2340 |
| gtaaccgttc | ctcatccgcg | acctgaaaaa | agaaccatgc | agaactaaa | aatgaaagcc | 2400 |
| cgcggacaag | tcacctggaa | agacaaaatc | agacaagccg | tcgatacaac | catgcgagaa | 2460 |
| gctcatatta | gcgattttaa | gagctttaaa | gagaaacttg | gtgaactagc | cgtcaatgtc | 2520 |
| attgaacgtg | gcagagacct | cacatatact | ctcacaggca | ctgattataa | atcacggggc | 2580 |

-continued

```
gcaaaactcg gagaggatta caaaaaggag accattttt atgagctgga cagaagaaac    2640
caattacagt acggaacaag tcgacaacga caaggtcgcg cttggcttga aggacgtgga    2700
gaacgccttg aacaagaaca acgcgctcgt caaaaccttg caaaaagagc agaagaccta    2760
caaagaagaa ctctcgaaag cactgaacaa tcaattcaac caagccatca acgacctcaa    2820
aaatcaaaag aaagaggact gggagggcct agcctctaat ttcgttaatc gcctcaatga    2880
cagcactaaa gaaatcacga atagccagct tgaaacggca caagaggaga tagacaagaa    2940 cttttgcacaa aaagaacaac gcttaaataa ccttgttttt aacattgaga gcgccgaaca    3000
agccttaaat tttctaaata acagaatcaa tcacatcaaa tcaaccgaaa gattgcagaa    3060
acaaaagcag ttctttcaag aaatcgtctt tattttgggc gcaatcatgg caagcctcgg    3120
aacattactc ttggtctttg cctttttgttc tgcccttat ggctttgggt ggcattccat    3180
ttggaactgg aaacaaatta ctccagtcta tgatgctcca accttcaaa aaggattatt    3240 tatcgtcatt aaagccattt taagtcttct attcttcatt tttggggtac tcgttatgtt    3300 tttcccttg gcgatttacc acaaattcct aaatagaatc aaaaatagtt acagaggttt    3360 tggggatgg ctcaataaag tattcatcag aaagtaagac agttttctg tcttttttt     3420 attgatcact tcgcaaaatt cgcgagcaca aaaattaaag ataatgcaaa ttaaaaattt    3480
cgtgttgtga gccttggcga acttttcctt ttggcaacct cggagagtgg gggaattttt    3540
gcgaaagcaa aaggggca aagcccctta aaatgctttt gggaaaatc tatgatttt        3600 gtccttttta aacctcttt tcagaaggg gggaaattta aaaatgagg ctgaaaatc        3660 cgagggtctc ttttatattt cttttataaa tcttttaaac ctcttttagg gggctgggaa    3720
acgttgatat cactagcgtg aagcgttggt tacatacccc taaatagggt actacatacc    3780
cctaaatagg gtactacata cccctaaata gggtactaca tacccctaaa tagggcgaga    3840
aagtttataa ccccttttta gggtacttca tttttttata acccttattt agggtacttc    3900
atttttttat aaccctttatt tagggtgaca aaaaccccg ttataaaggt gttttgcttt    3960 tataaccct ttttagggtg cctctataac ccttatttag ggtagatatt ttatataaaa    4020
attgctataa tttttataac cctaaaggga taaagaaagg aagtataatg gttcatgaaa    4080
tagtacaata tcacaacgat tttaacactg ttccacttag aggatttaat gaacgagaac    4140
gtagaattgt aatggcatta cttcatcaag taaaaaataa agatgtcgaa gtggttcaat    4200
tagactttga tactttgcgt ggattatctg gttggaatga tactttagct aaatctgaaa    4260
attccaatgc taaatttaac cggtatcttg aaaacttgtc tgataaaatt atgacattac    4320
gaggaactct aagaagtgaa gatggtttgc aagtagttaa atttagtctc tttccaacat    4380
ttattattga tgggaaaaat actatgaccc taaaagttca aattaacccct acttttaaat    4440 atcttactaa tatctttgat atgttcacag cttttgaatt agatgattat aatcgtatga    4500
acactagcta tgggcaagaa ctttatagat tattaaaaca gtatcgaaca tctggttttt    4560
atcgtgtgaa gatagaggac ttgcgacatc tattatcagt tcctgaaagc tataccaatg    4620
caaaaatgga tcaaaagta ttttcaaaaa ctactgtaac tgaccttacc aatgcttttc    4680
cgaattttaa aatcaaacaa gaacgaggca ctggtcgagg tcgaccaata attggttaca    4740
ccttcacttt cgataaagaa gccccaaata agtatgagct agaccgcaaa aagcaagaac    4800
aaattgccca ttttggaaa tcaaatgacc ctgagccaat gcctaatgca gttgctcaaa    4860
cggaatatca aaatcctgaa ttacgaaaag aaaaagaaga gctcgaaaaa cataacgcta    4920
```

-continued

| | |
|---|---:|
| gttttggaga cttattaaag ggctggttca aaaaatagat aaatatgaaa tttaaaaaga | 4980 |
| aaaattatac tcctcaagta gatgaaaaag actgtggttg tgcggcatta tcaatgattt | 5040 |
| taaaaactta cgaaacagaa aagtcacttg cttcattttt attgaatcag aggataaaaa | 5100 |
| tgcataaagt atttgaaaaa attattacaa ttttttttgc cttttttta tttttcattt | 5160 |
| ctcaaatccc aatatactac gtaaattata aaaataaaga aaataattta tatggaatat | 5220 |
| caaataaaat atcattacct tttatattta ttgctttatt tgttattata atagcagttg | 5280 |
| ctctaggtaa aaaaagagga ttttaccatc attcgaagaa acattagaa ttc | 5333 |

<210> SEQ ID NO 2
<211> LENGTH: 2590
<212> TYPE: DNA
<213> ORGANISM: Lactococcus lactis

<400> SEQUENCE: 2

| | |
|---|---:|
| cataaatcta ctctatgcta aaaacaaaaa tcttatttaa taattatatt ctcatttcta | 60 |
| tctgtagtgt ttattaatat ttttgaaaga taaagataga aagaattaat cattaaacta | 120 |
| tcagaaatta caaaaatggc tagcatactg cttagccatt tttatttaa ttctgcgaac | 180 |
| cgagggggtt aagggtggag ctttgctccc ccttacaagc gccacaatag ccacgaagtg | 240 |
| gctagcttgt gggttgcttg ccaagacttt atctttattc tagcttttga gggtcgagct | 300 |
| tgagcgtcgg acacgaaaag tgctagaata aagtatgga cggaacgtcc atggaaaggc | 360 |
| gggggttatg agcgaacact taaatatggc tagcattaaa agaaacaac caaatcgaaa | 420 |
| agaacgaaaa caaataagtt tcagagtgag cgaaccggaa tatttaaacc ttgagcgctc | 480 |
| agcgaaagtc ttaaatattt cggtgccggc ttttgtcaaa aagaaggcac aaggcgctcg | 540 |
| tgtcgtcgca cctaaaatta atccagacga ttcaaaagaa atggctcgcc agttggcagc | 600 |
| acttggcaat aacgtgaatc aactcgctaa aagggtcaat cagattgaat ttgcggataa | 660 |
| ggacacgcaa gagcgcctat cagccgattt aaggcgcacc ttacacggtc tgggggaaat | 720 |
| atggcgacaa ctcacataaa acgctcaaat ggcgcttcta gactcgtcaa ctacgctgaa | 780 |
| aaaagagcgg ttcaaaaaga cggctataat ttagacattg agtatgccaa atctgaactc | 840 |
| aaacaagttc gagaaattta cggaaacaaa ggggcaacgc aagcctacgc ttcaagagtg | 900 |
| gcattctctc cgaaagaatt tgaccctaaa aatgtaaaag accaactaaa ggcactagaa | 960 |
| atcgctaaag aaatctattc aaccgcctat cccaaccaac aaatcgcaat gtatgttcac | 1020 |
| aacgacaccg attccctcca cgttcacgcc gtgattggcg ccattaacct actaacaggt | 1080 |
| aaaaaaatgc acggcaattg caagaataac cgtgaaaggc tcgttaaaat aacggataaa | 1140 |
| gtcgtggaga acatggctt aaccgtaacc gttcctcatc cgcgacctga aaaagaacc | 1200 |
| atggcagaac taaaaatgaa agcccgcgga caagtcacct ggaaagacaa atcagacaa | 1260 |
| gccgtcgata caaccatgcg agaagctcat attagcgatt ttaagagctt taagagaaa | 1320 |
| cttggtgaac tagccgtcaa tgtcattgaa cgtggcagag acctcacata tactctcaca | 1380 |
| ggcactgatt ataaatcacg gggcgcaaaa ctcggagagg attacaaaaa ggagaccatt | 1440 |
| ttttatgagc tggacagaag aaaccaatta cagtacggaa caagtcgaca acgcaaggt | 1500 |
| cgcgcttggc ttgaaggacg tggagaacgc cttgaacaag aacaacgcgc tcgtcaaaac | 1560 |
| cttgcaaaaa gagcagaaga cctacaaaga agaactctcg aaagcactga caatcaatt | 1620 |
| caaccaagcc atcaacgacc tcaaaaatca aagaaagag gactggagg cctagcctc | 1680 |
| taatttcgtt aatcgcctca atgacagcac taaagaaatc acgaatagcc agcttgaaac | 1740 |

```
ggcacaagag gagatagaca agaactttgc acaaaaagaa caacgcttaa ataaccttgt      1800
ttttaacatt gagagcgccg aacaagcctt aaattttcta aataacagaa tcaatcacat      1860
caaatcaacc gaaagattgc agaaacaaaa gcagttcttt caagaaatcg tctttatttt      1920
gggcgcaatc atggcaagcc tcggaacatt actcttggtc tttgccttttt gttctgccct      1980 ttatggcttt gggtggcatt ccatttggaa ctggaaacaa attactccag tctatgatgc      2040
tccaaccttt caaaaggat tatttatcgt cattaaagcc attttaagtc ttctattctt       2100 cattttggg gtactcgtta tgttttccc cttggcgatt taccacaaat tcctaaatag        2160
aatcaaaaat agttacagag gttttggggg atggctcaat aaagtattca tcagaaagta     2220
agacagtttt tctgtctttt ttttattgat cacttcgcaa aattcgcgag cacaaaaatt     2280
aaagataatg caaattaaaa atttcgtgtt gtgagccttg gcgaactttt ccttttggca     2340
acctcggaga gtgggggaat ttttgcgaaa gcaaaagggg ggcaaagccc cttaaaatgc     2400
ttttgggaaa aatctatgat ttttgtcctt tttaaacctc tttttttcaga aggggggaaa    2460 tttaaaaaat gaggctgaaa aatccgaggg tctcttttat atttcttta taaatctcttt    2520 aaacctcttt tagggggctg ggaaacgttg atatcactag cgtgaagcgt tggttacata    2580
cccctaaata                                                              2590

<210> SEQ ID NO 3
<211> LENGTH: 31
<212> TYPE: DNA
<213> ORGANISM: Artificial sequence
<220> FEATURE:
<223> OTHER INFORMATION: Description of the artificial
      sequence:oligonucleotide

<400> SEQUENCE: 3
tacatacgcg tctcatatat actttagatt g                                      31

<210> SEQ ID NO 4
<211> LENGTH: 31
<212> TYPE: DNA
<213> ORGANISM: Artificial sequence
<220> FEATURE:
<223> OTHER INFORMATION: Description of the artificial
      sequence:oligonucleotide

<400> SEQUENCE: 4
tacatacgcg tgacttagaa gcaaacttaa g                                      31

<210> SEQ ID NO 5
<211> LENGTH: 31
<212> TYPE: DNA
<213> ORGANISM: Artificial sequence
<220> FEATURE:
<223> OTHER INFORMATION: Description of the artificial
      sequence:oligonucleotide

<400> SEQUENCE: 5
ttaaatgatc agagctccac cgcggtggcg g                                      31

<210> SEQ ID NO 6
<211> LENGTH: 31
<212> TYPE: DNA
<213> ORGANISM: Artificial sequence
<220> FEATURE:
<223> OTHER INFORMATION: Description of the artificial
      sequence:oligonucleotide
```

-continued

```
<400> SEQUENCE: 6
tattttgatc agaacaaaag ctgggtaccg g                                      31

<210> SEQ ID NO 7
<211> LENGTH: 31
<212> TYPE: DNA
<213> ORGANISM: Artificial sequence
<220> FEATURE:
<223> OTHER INFORMATION: Description of the artificial
      sequence:oligonucleotide

<400> SEQUENCE: 7
atttatgatc atttccagtc gggaaacctg t                                      31

<210> SEQ ID NO 8
<211> LENGTH: 31
<212> TYPE: DNA
<213> ORGANISM: Artificial sequence
<220> FEATURE:
<223> OTHER INFORMATION: Description of the artificial
      sequence:oligonucleotide

<400> SEQUENCE: 8
aattttgatc aagtatacct ataatttat c                                       31

<210> SEQ ID NO 9
<211> LENGTH: 31
<212> TYPE: DNA
<213> ORGANISM: Artificial sequence
<220> FEATURE:
<223> OTHER INFORMATION: Description of the artificial
      sequence:oligonucleotide

<400> SEQUENCE: 9
tatgtgaatt cgacttagaa gcaaacttaa g                                      31

<210> SEQ ID NO 10
<211> LENGTH: 31
<212> TYPE: DNA
<213> ORGANISM: Artificial sequence
<220> FEATURE:
<223> OTHER INFORMATION: Description of the artificial
      sequence:oligonucleotide

<400> SEQUENCE: 10
tatgtgaatt cagtatacct aataatttat c                                      31

<210> SEQ ID NO 11
<211> LENGTH: 29
<212> TYPE: DNA
<213> ORGANISM: Artificial sequence
<220> FEATURE:
<223> OTHER INFORMATION: Description of the artificial
      sequence:oligonucleotide

<400> SEQUENCE: 11
tataagaatt ccgctcgtgt cgtcgcacc                                         29

<210> SEQ ID NO 12
<211> LENGTH: 29
<212> TYPE: DNA
<213> ORGANISM: Artificial sequence
<220> FEATURE:
<223> OTHER INFORMATION: Description of the artificial
      sequence:oligonucleotide

<400> SEQUENCE: 12
```
tataagaatt ccataaatct actctatgc                                              29

<210> SEQ ID NO 13
<211> LENGTH: 30
<212> TYPE: DNA
<213> ORGANISM: Artificial sequence
<220> FEATURE:
<223> OTHER INFORMATION: Description of the artificial
      sequence:oligonucleotide

<400> SEQUENCE: 13
tataagaatt cgtagatgag attttaaagc                                             30

<210> SEQ ID NO 14
<211> LENGTH: 29
<212> TYPE: DNA
<213> ORGANISM: Artificial sequence
<220> FEATURE:
<223> OTHER INFORMATION: Description of the artificial
      sequence:oligonucleotide

<400> SEQUENCE: 14
tattagaatt ctatttaggg gtatgtaac                                              29

<210> SEQ ID NO 15
<211> LENGTH: 32
<212> TYPE: DNA
<213> ORGANISM: Artificial sequence
<220> FEATURE:
<223> OTHER INFORMATION: Description of the artificial
      sequence:oligonucleotide

<400> SEQUENCE: 15
tattagaatt ccgtgatttc tttagtgctg tc                                          32

<210> SEQ ID NO 16
<211> LENGTH: 31
<212> TYPE: DNA
<213> ORGANISM: Artificial sequence
<220> FEATURE:
<223> OTHER INFORMATION: Description of the artificial
      sequence:oligonucleotide

<400> SEQUENCE: 16
tatataagct tagtataacct aataatttat c                                          31

<210> SEQ ID NO 17
<211> LENGTH: 29
<212> TYPE: DNA
<213> ORGANISM: Artificial sequence
<220> FEATURE:
<223> OTHER INFORMATION: Description of the artificial
      sequence:oligonucleotide

<400> SEQUENCE: 17
tatataagct tcacttcgca aaattcgcg                                              29

<210> SEQ ID NO 18
<211> LENGTH: 29
<212> TYPE: DNA
<213> ORGANISM: Artificial sequence
<220> FEATURE:
<223> OTHER INFORMATION: Description of the artificial
      sequence:oligonucleotide

<400> SEQUENCE: 18

```
                                        -continued tatataagct tgagggtcga gcttgagcg                                      29

<210> SEQ ID NO 19
<211> LENGTH: 31
<212> TYPE: DNA
<213> ORGANISM: Artificial sequence
<220> FEATURE:
<223> OTHER INFORMATION: Description of the artificial
      sequence:oligonucleotide

<400> SEQUENCE: 19
tatataagct tcactcttta tatgctaata c                                   31

<210> SEQ ID NO 20
<211> LENGTH: 20
<212> TYPE: DNA
<213> ORGANISM: Artificial sequence
<220> FEATURE:
<223> OTHER INFORMATION: Description of the artificial
      sequence:oligonucleotide

<400> SEQUENCE: 20
aggtttcccg actggaaatg                                                20

<210> SEQ ID NO 21
<211> LENGTH: 31
<212> TYPE: DNA
<213> ORGANISM: Artificial sequence
<220> FEATURE:
<223> OTHER INFORMATION: Description of the artificial
      sequence:oligonucleotide

<400> SEQUENCE: 21
tacgtgaatt cagttttaaa tcaatctaaa g                                   31

<210> SEQ ID NO 22
<211> LENGTH: 31
<212> TYPE: DNA
<213> ORGANISM: Artificial sequence
<220> FEATURE:
<223> OTHER INFORMATION: Description of the artificial
      sequence:oligonucleotide

<400> SEQUENCE: 22
tacgtggatc catcggcata atcgttaaaa c                                   31

<210> SEQ ID NO 23
<211> LENGTH: 31
<212> TYPE: DNA
<213> ORGANISM: Artificial sequence
<220> FEATURE:
<223> OTHER INFORMATION: Description of the artificial
      sequence:oligonucleotide

<400> SEQUENCE: 23
tacgtgaatt cagaagaacc cttaactaaa c                                   31
```

DNA SEQUENCES CONTAINING A CONJUGATIVE TRANSFER MECHANISM

This application is a 371 of PCT/FR99/03297, filed Dec. 12, 1999.

The present invention relates to novel DNA sequences capable of being transferred by conjugation, to plasmids containing these sequences, to bacteria containing these DNA sequences or these plasmids, and to the use of these bacteria.

Lactic acid bacteria are involved in the production and preservation of a large number of food products, such as cheese, butter, yogurt, sausage or sauerkraut, among which dairy products are of particular importance. The transformation of milk by lactic acid bacteria is being carried out in ever-larger vats. An understanding of the mechanisms of transfer of genetic material is essential for improving the strains of lactic acid bacteria used in these fermentations. The different mechanisms of transfer of genetic material are transformation, transduction, protoplast fusion and conjugation. Transformation consists in causing genetic material to enter a bacterium by natural competence, conversion of the cells to protoplasts or electropermeation of the cells.

Transduction consists in causing genetic material to enter a bacterium by means of a bacteriophage vector.

Protoplast fusion consists in converting two types of cells to protoplasts so that, after contact, genetic material passes from one strain into the other strain.

Conjugation consists in bringing two types of cells into contact so that genetic material passes from one strain into the other strain by virtue of natural conjugative genes.

Two distinct cases are possible: either the plasmid possesses all the genes involved in conjugation and said plasmid itself passes into the receptor strain, or the plasmid possesses only the genetic components sufficient for its transfer, the other components being present e.g. on another plasmid (Mobilization of the relaxable *Staphylococcus aureus* plasmid pC221 by the conjugative plasmid pG01 involves three pC221 loci, S. J. Projan and G. L. Archer, J. Bacteriol. 1989; 171: 1841–1845). The latter situation has an advantage: if the plasmid is transferred to a receptor strain without the conjugative plasmid, it will be unable to be transferred again, its dissemination thereby being prevented. This technique of conjugative plasmid transfer also has the advantage of introducing genetic material into strains in which this is difficult using the transfer techniques described above.

A few studies have already made it possible to demonstrate conjugative systems in lactic acid bacteria:

Genetic analysis of regions of the *Lactococcus lactis* subsp. lactis plasmid pRS01 involved in conjugative transfer, D. A. Mills, C. K. Choi, G. M. Dunny and L. L. McKay, Applied and Environ. Microbiol. 1994; 60 (12): 4413–4420;

Splicing of a group II intron involved in the conjugative transfer of pRS01 in lactococci, D. A. Mills, L. L. McKay and G. M. Dunny, J. Bacteriol. 1996; 178 (12): 3531–3538.

In the present patent application, a DNA sequence is described which comprises at least one conjugative transfer mechanism; this DNA sequence comprises a functional part of 5333 bp present in the strain *Lactococcus lactis* FL877 deposited on Sep. 30, 1998 in the CNCM (Collection Nationale de Cultures de Microorganismes) under no. I-2082.

This DNA sequence of 5333 bp (SEQ ID No: 1) was isolated from the plasmids contained in the strain FL877.

More precisely, the fragment of 5333 base pairs (bp) was isolated by total digestion, with the restriction enzyme EcoRI, of the plasmids contained in the strain *Lactococcus lactis* FL877. This fragment carries one or more conjugative transfer mechanisms and is capable of being transferred to another strain, especially another strain of *L. lactis*, for example from the strain MG1363 (GASSON M. J., J. Bacteriol. 1983; 154: 1–9). This fragment also carries a system of functional replication in *L. lactis*.

From the nucleotide sequence SEQ ID No: 1, the Applicant then isolated a DNA sequence of 2590 bp, which alone confers on a plasmid the property of being transferred to another strain by conjugation, especially from the strain MG1363.

This sequence of 2590 bp (SEQ ID No: 2) can be obtained by the PCR (polymerase chain reaction) method with the aid of appropriate oligonucleotides.

Thus, according to a first feature, the present invention relates to a nucleic acid sequence capable of being transferred by conjugation, which comprises the sequence SEQ ID No: 2, its complementary strand or any sequence derived from said sequence or from its complementary strand by virtue of the degeneracy of the genetic code.

The invention preferably relates to a nucleic acid sequence capable of being transferred by conjugation, said sequence being selected from:

a) the nucleotide sequence of 5333 bp (SEQ ID No: 1) or its complementary strand;

b) any sequence hybridizing with the sequence a) under strict conditions; or c) sequences derived from the sequences a) and b) by virtue of the degeneracy of the genetic code.

The invention relates more particularly to a nucleic acid sequence selected from:

a) the nucleotide sequence of 2590 bp (SEQ ID No: 2) or its complementary strand;

b) any sequence hybridizing with the sequence a) under strict conditions; or c) sequences derived from the sequences a) and b) by virtue of the degeneracy of the genetic code.

According to the present invention, "hybridizing under strict conditions" is understood as meaning hybridization under the following stringency conditions: 42° C. in a 20 mM sodium phosphate buffer (pH 6.5) containing 50% of formamide, 5×SSC, 1×Denhardt's, 0.1% of SDS and 100 μg/ml of RNA, and then washing at 60° C. in a buffer containing 0.1×SSC and 0.1% of SDS.

The invention further relates to DNA sequences which have a high degree of homology with the above DNA sequences. A high degree of homology means a homology (ratio of the identical nucleotides to the total number of nucleotides) of at least 70%, preferably of at least 80% and particularly preferably of at least 90% of the nucleotide sequences when they are aligned according to the maximum homology by the optimum sequence alignment method of Needleman and Wunsch, J. Mol. Biol. 1970; 48: 443–453. This method is used especially in the UWGCG software of the University of Wisconsin: Devereux et al., Nucl. Ac. Res. 1984; 12: 8711–8721-option GAP.

The invention further relates to plasmids transformed with one of the DNA sequences according to the invention. These plasmids can be e.g. plasmid pLDP1 (PREVOTS F. et al., FEMS Microbiol. Lett. 1996; 142: 295–299) and plasmid pLAB510 derived from pPF107-3. (PREVOTS F. et al., FEMS Microbiol. Lett. 1998; 159: 331–336), into which one of the DNA sequences according to the invention has been cloned by the conventional techniques well known to those skilled in the art.

The invention further relates to bacteria, especially lactic acid bacteria, preferably belonging to the species Lactococcus lactis, which contain at least one DNA sequence or one plasmid as defined above.

These bacteria can be used for the conjugative transfer of genetic material, especially genetic material of industrial interest, to a strain of industrial interest. The conjugative transfer mechanism can be carried by a plasmid or by another part of the bacterial genome.

In particular, these bacteria can be used for the conjugative transfer of properties such as phage resistance, the ability to ferment lactose, proteolysis, peptidolysis and bacteriocin production, and of genes coding for proteins of pharmaceutical interest, to strains of industrial interest, particularly in the dairy industry, but also in the pharmaceutical industry.

The strains of industrial interest which can advantageously receive genetic material with the aid of the DNA sequences according to the invention, or a plasmid containing them, are e.g. the strains L. lactis ssp lactis and L. lactis ssp cremoris.

The invention therefore also relates to these strains of industrial interest into which said genetic material has been integrated.

The invention will be understood more clearly with the aid of the Examples below, which include experimental results and a discussion thereof Some of these Examples relate to experiments performed for the purpose of carrying out the invention, while others are Examples of implementation of the invention, which are of course given purely by way of illustration.

A large part of all the techniques described in these Examples, which is well known to those skilled in the art, is described in detail in the work by Sambrook, Fritsch and Maniatis entitled: "Molecular Cloning; a laboratory manual", published in 1989 by Cold Spring Harbor Press, New York (2nd edition).

The following description will be understood more clearly with the aid of FIGS. 1 and 2 below, which show:

The following abbreviations are used in this Figure:

Rep+ or –: fragment replicative (+) or non-replicative (–) in MG1363

Rel+ or –: relaxation (+) or non-relaxation (–) in MG1363

Mob+ or –: high efficacy (+) or low efficacy (–) of transfer of the plasmid from MG1363 to LM2301

In addition, the numbers above the sequences represent the base position on plasmid pLAB500.

Figure 2:
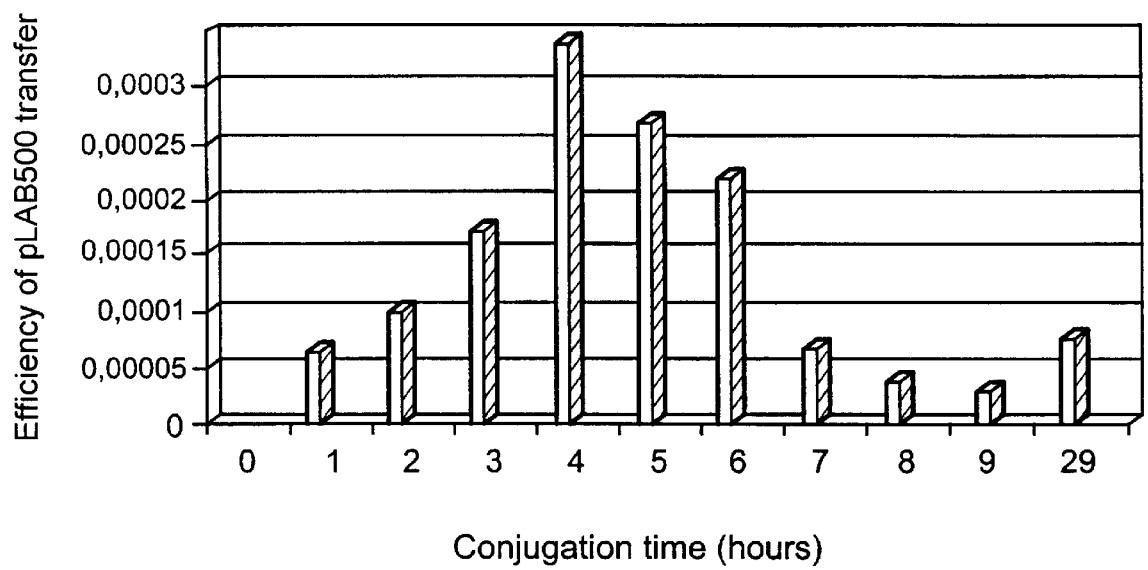

FIG. 2: Kinetics of transfer of plasmid pLAB500

EXAMPLE 1

Sequence of the 5333 bp Fragment

The PCR (polymerase chain reaction) technique, described e.g. in the work by Maniatis cited above, makes it possible to amplify a DNA fragment located between 2 suitably chosen oligonucleotides. This amplified DNA can easily be ligated to itself if restriction sites are provided by the oligonucleotides. In fact, the sequences of these oligonucleotides can contain, at their 5' end, a heterologous part of the DNA to be amplified, consisting e.g. of 10 to 12 base pairs, six of which constitute a restriction site.

The following oligonucleotides were used to construct an erythromycin resistance gene flanked on either side by an EcoRI restriction site:

oligonucleotide 1:
  TACATACGCGTCTCATATATACTTTAGATTG (SEQ ID No: 3)
oligonucleotide 2:
  TACATACGCGTGACTTAGAAGCAAACTTAAG (SEQ ID No: 4)
oligonucleotide 3:
  TTAAATGATCAGAGCTCCACCGCGGTGGCGG (SEQ ID No: 5)
oligonucleotide 4:
  TATTTTGATCAGAACAAAAGCTGGGTACCGG (SEQ ID No: 6)
oligonucleotide 5:
  ATTTATGATCATTTCCAGTCGGGAAACCTGT (SEQ ID No: 7)
oligonucleotide 6:
  AATTTTGATCAAGTATACCTAATAATTTATC (SEQ ID No: 8)
oligonucleotide 7:
  TATGTGAATTCGACTTAGAAGCAAACTTAAG (SEQ ID No: 9)
oligonucleotide 8:
  TATGTGAATTCAGTATACCTAATAATTTATC (SEQ ID No: 10)

Using oligonucleotides 5 and 1, a 1.1 kb fragment containing the origin of replication could be amplified by PCR from plasmid pRC1 (LE BOURGEOIS P. et al., Gene 1992; 111: 109–114).

Using oligonucleotides 2 and 6, a 1 kb fragment containing the erythromycin resistance gene could be amplified by PCR from plasmid pRC1.

These two fragments were digested with BclI and MluI and ligated and were then used to transform E. coli TG1 (GIBSON T. J., Studies on the Epstein-Barr genome, PhD thesis, Cambridge University, Cambridge, UK, 1984) to give plasmid pRC1int.

Using oligonucleotides 3 and 4, a 0.3 kb fragment containing several unique restriction sites could be amplified by PCR from plasmid pRC1. This fragment was digested with BclI and then ligated to plasmid pRC1int, itself digested with BclI. This novel plasmid, containing the erythromycin resistance gene, an origin of functional replication in E. coli but not in L. lactis, and several unique restriction sites, was called pRC1N.

Using oligonucleotides 7 and 8, a 939 bp fragment containing the erythromycin resistance gene was amplified by PCR from plasmid pRC1N. This fragment was subsequently digested with EcoRI and then ligated to all the plasmids of the strain L. lactis FL877, which had previously been extracted and digested with the restriction enzyme EcoRI. The strain MG1363 was transformed by this ligation mixture. All the resulting erythromycin resistant clones were used as the donor strain in a conjugation experiment (PREVOTS F. et al., FEMS Microbiol. Lett. 1994; 117: 7–14) with the receptor strain LM2301 (WALSH P. M. et al., J. Bacteriol. 1981; 146: 937–944), which is resistant to streptomycin and sensitive to erythromycin. The transconjugants are selected for their resistance to these two antibiotics. The plasmids which had been transferred to this strain LM2301 by conjugation were extracted and used to retransform the strain MG1363. Plasmid pLAB500 of 6.3 kb was isolated in this way; it was capable of replicating in both the strains LM2301 and MG1363 and capable of being transferred from the strain MG1363 to the strain LM2301 with a high efficiency.

After digestion with the restriction enzyme EcoRI, this plasmid gives 2 fragments of 1 kb and 5.3 kb. The first fragment contains the erythromycin resistance gene. The last fragment of 5333 bp was entirely sequenced by the method of Sanger et al. (PNAS-USA 1977; 14: 5463).

Figure 1:
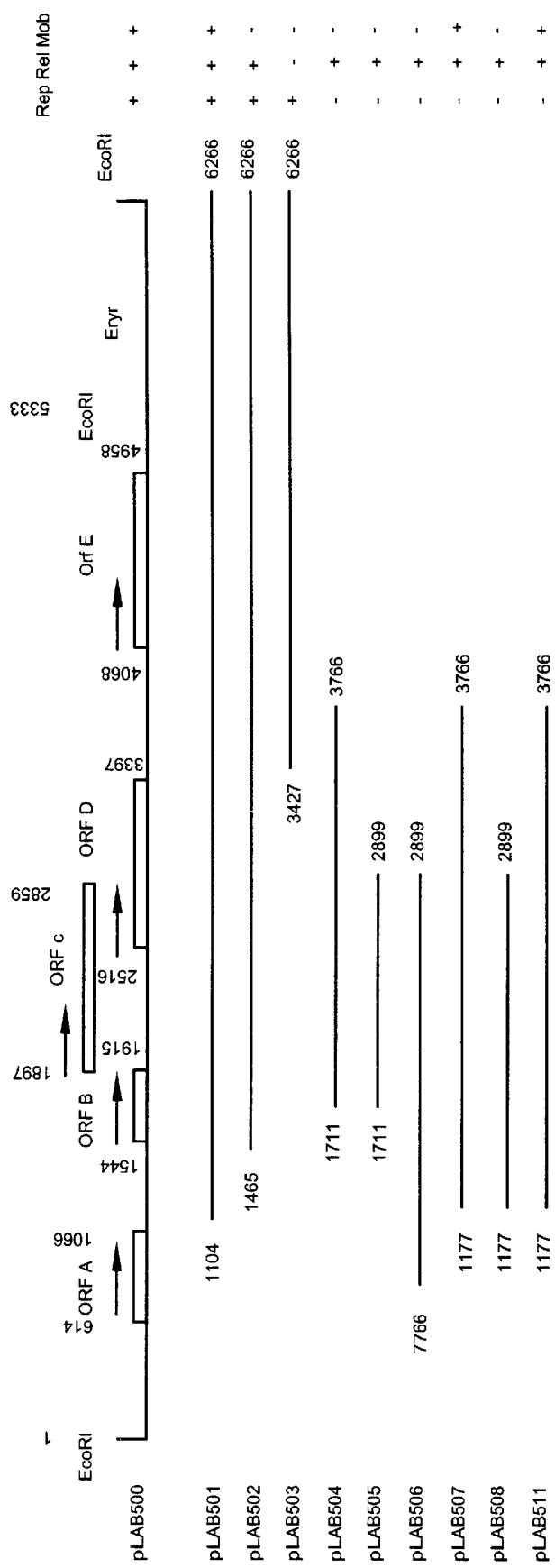
FIG. 1: Subcloning of internal fragments of plasmid pLAB500

Analysis of the sequence showed that the 5333 bp fragment possesses 5 complete open reading frames of more than 150 bp (FIG. 1).

EXAMPLE 2

Reduction of the Size of Plasmid pLAB500

The PCR technique was applied in order to determine which of the open reading frames are involved in conjugation and which are involved in replication of the plasmid.

9 oligonucleotides, each comprising an EcoRI or HindIII restriction site, were synthesized for this purpose. These oligonucleotides have the following sequences:

oligonucleotide 9:
  TATAAGAATTCCGCTCGTGTCGTCGCACC (SEQ ID No: 11)
oligonucleotide 10:
  TATAAGAATTCCATAAATCTACTCTATGC (SEQ ID No: 12)
oligonucleotide 11:
  TATAAGAATTCGTAGATGAGATTTTAAAGC (SEQ ID No: 13)
oligonucleotide 12:
  TATTAGAATTCTATTTAGGGGTATGTAAC (SEQ ID No: 14)
oligonucleotide 13:
  TATTAGAATTCCGTGATTTCTTTAGTGCTGTC (SEQ ID No: 15)
oligonucleotide 14:
  TATATAAGCTTAGTATACCTAATAATTTATC (SEQ ID No: 16)
oligonucleotide 15:
  TATATAAGCTTCACTTCGCAAAATTCGCG (SEQ ID No: 17)
oligonucleotide 16:
  TATATAAGCTTGAGGGTCGAGCTTGAGCG (SEQ ID No: 18)
oligonucleotide 17:
  TATATAAGCTTCACTCTTTATATGCTAATAC (SEQ ID No: 19)

Using oligonucleotides 14 and 15, a DNA fragment of 2846 bp, containing the erythromycin resistance gene and ORF E in the form of a HindIII-HindIII fragment, could be amplified by virtue of the restriction sites provided by the oligonucleotides, enabling this fragment to be ligated to itself.

Likewise, a DNA fragment of 4808 bp, containing the erythromycin gene and ORF B, C, D and E, could be amplified using oligonucleotides 14 and 16.

Finally, a DNA fragment of 5169 bp, containing the erythromycin gene and ORF B, C, D and E, could be amplified using oligonucleotides 14 and 17.

These DNA fragments were amplified by PCR from a preparation of plasmid pLAB500 with the enzyme ELONGASE® (BRL).

The PCR products were purified by extraction with phenol/chloroform, precipitated with ethanol, digested with the restriction enzyme HindIII and ligated to themselves. Cloning of these fragments onto themselves yielded plasmids pLAB501, pLAB502 and pLAB503. These plasmids were constructed in the strain MG1363. Their ability to replicate in this strain indicates that ORF E codes for a protein involved in replication of the plasmid. Moreover, over 230 amino acids, this protein shows a homology of 21.7% with the protein RepE involved in replication of the F factor of E. coli.

These plasmids were then tested for their ability to be transferred to the strain LM2301 by conjugation. Plasmids pLAB502 and pLAB503 have a comparable transfer efficiency to that of pLDP1, the negative control. It can therefore be said that these plasmids do not possess all the DNA necessary for their conjugative transfer. On the other hand, pLAB501 has a comparable conjugative transfer efficiency to that of pLAB500, so all the DNA necessary for the conjugative transfer of pLAB500 must be present in pLAB501.

EXAMPLE 3

Subcloning of pLAB500 fragments into plasmid pLDP1

A fragment containing ORF C and D in the form of an EcoRI-EcoRI fragment of 2068 bp could be amplified by PCR using oligonucleotides 9 and 12.

A fragment containing ORF C in the form of an EcoRI-EcoRI fragment of 1201 bp could be amplified by PCR using oligonucleotides 9 and 13.

A fragment containing ORF B and C in the form of an EcoRI-EcoRI fragment of 2136 bp could be amplified by PCR using oligonucleotides 11 and 13.

A fragment containing ORF B, C and D in the form of an EcoRI-EcoRI fragment of 2602 bp could be amplified by PCR using oligonucleotides 10 and 12.

A fragment containing ORF B and C in the form of an EcoRI-EcoRI fragment of 1735 bp could be amplified by PCR using oligonucleotides 10 and 13.

After digestion with the enzyme EcoRI, each of these fragments was cloned into pLDP1 to give plasmids pLAB504, pLAB505, pLAB506, pLAB507 and pLAB508 respectively. Among these plasmids, only pLAB507 was transferred with a significant efficiency, which was better than that of the other plasmids but nevertheless not as good as that of pLAB500. It can therefore be said that ORF B, C and D are necessary for conjugative transfer.

EXAMPLE 4

Subcloning of a pLAB500 Fragment into pLAB510

The following oligonucleotides were used in this subcloning:
oligonucleotide 18:
  AGGTTTCCCGACTGGAAATG (SEQ ID No: 20)
oligonucleotide 19:
  TACGTGAATTCAGTTTTAAATCAATCTAAAG (SEQ ID No: 21)
oligonucleotide 20:
  TACGTGGATCCATCGGCATAATCGTTAAAAC (SEQ ID No: 22)
oligonucleotide 21:
  TACGTGAATTCAGAAGAACCCTTAACTAAAC (SEQ ID No: 23)

Plasmid pLDP1 is transferred by conjugation from MG1363 to LM2301 with a low but non-zero efficiency. To eliminate the contribution of this plasmid in the transfer, the PCR fragment obtained with oligonucleotides 10 and 12 was cloned into another plasmid.

The erythromycin resistance gene was first amplified by PCR from plasmid pRClN and oligonucleotides 18 and 19, and then digested with the restriction enzymes BamHI and EcoRI. Using oligonucleotides 20 and 21, a replicative fragment of plasmid pPF107-3 (GenBank access number: Y12675) was amplified from the total DNA of the strain I-942 (deposited in the CNCM on Apr. 12, 1990) and then digested with the restriction enzymes BamHI and EcoRI. These two PCR fragments were ligated and used to transform MG1363. The novel plasmid obtained, called pLAB510, was digested with EcoRI and then ligated to the fragment obtained with oligonucleotides 10 and 12 by PCR amplification from plasmid pLAB500, and digested with EcoRI. This ligation was used to transform MG1363. This novel plasmid, pLAB511, was tested for its ability to be transferred from MG1363 to LM2301 (Table 1). It can be seen that this novel plasmid pLAB511 is indeed transferable between these two strains by conjugation.

TABLE 1

Conjugative transfer efficiency

| Plasmid | ORF | Efficiency | Relative efficiency |
|---|---|---|---|
| pLAB500 | A,B,C,D,E | $8.3 \times 10^{-4}$ | 100 |
| pLAB501 | B,C,D,E | $7.1 \times 10^{-4}$ | 85 |
| pLAB502 | B,C,D,E | $1.1 \times 10^{-7}$ | 0.01 |
| pLAB503 | E | $<5 \times 10^{-9}$ | <0.0006 |
| pLAB504 | C,D | $1 \times 10^{-7}$ | 0.01 |
| pLAB505 | C,D | $5.7 \times 10^{-8}$ | 0.007 |
| pLAB506 | B,C | $5.7 \times 10^{-8}$ | 0.007 |
| pLAB507 | B,C,D | $4.5 \times 10^{-5}$ | 5.4 |
| pLAB508 | B,C | $4.2 \times 10^{-7}$ | 0.05 |
| pLDP1 | / | $9.2 \times 10^{-8}$ | 0.01 |
| pLAB510 | / | $<5 \times 10^{-9}$ | <0.0006 |
| pLAB511 | B,C,D | $1.3 \times 10^{-3}$ | 157 |

Efficiency=ratio of the number of transconjugants to the number of receptor cells.

Relative efficiency=ratio of the efficiency of conjugation for a given plasmid to the efficiency of conjugation for pLAB500×100.

ORF =complete open reading frames contained in the plasmid.

EXAMPLE 5

Demonstration of the relaxation conferred by different plasmids

Relaxation (formation of open circular forms of plasmids from supercoiled forms of plasmids) is involved in the transfer of certain plasmids (Plasmid-protein relaxation complexes in *Staphylococcus aureus*, R. Novick, J. Bacteriol. 1976; 127: 1177–1187). From comparisons with computerized data banks (GenBank), the protein deduced from ORF C shows a homology of 35.2% with Rlx, a relaxase from *Staphylococcus aureus*. It can therefore be assumed that this protein deduced from ORF C is also a relaxase. Plasmids pLAB500 to pLAB508, pLAB510, pLABS11 and pLDP1 were therefore extracted and deposited on agarose gel. After migration, among all these plasmids extracted from MG1363, only pLAB503, pLAB510 and pLDP1 do not have an open circular form, so ORF C is indeed involved in the relaxation of plasmids.

EXAMPLE 6

Kinetics of pLAB500 transfer

Conjugations between MG1363 containing pLAB500 and LM2301 were performed at different times in order to evaluate the point at which transfer took place. It is found (cf. Table 2 below and FIG. 2) that conjugation has already started after 1 hour and that the peak of transfer efficiency is reached after about 4 hours. Conjugations every 10 minutes between 0 and one hour also showed that no conjugation took place before one hour.

TABLE 2

Kinetics of pLAB500 transfer

| Conjugation time (hours) | Efficiency of conjugation |
|---|---|
| 0 | $<1.1 \times 10^{-8}$ |
| 1 | $6.6 \times 10^{-5}$ |
| 2 | $9.8 \times 10^{-5}$ |
| 3 | $1.7 \times 10^{-4}$ |
| 4 | $3.4 \times 10^{-4}$ |
| 5 | $2.7 \times 10^{-4}$ |
| 6 | $2.2 \times 10^{-4}$ |
| 7 | $6.7 \times 10^{-5}$ |
| 8 | $4.2 \times 10^{-5}$ |
| 9 | $3.0 \times 10^{-5}$ |
| 29 | $7.9 \times 10^{-5}$ |

Efficiency of conjugation=ratio of the number of transconjugants to the number of receptor cells.

What is claimed is:

1. An isolated nucleic acid sequence capable of being transferred by conjugation, which comprises the sequence SEQ ID No:2, or its complementary strand.

2. The isolated nucleic acid sequence according to claim 1 which is selected from the group consisting of:
   a) the nucleotide sequence of 5333 bp (SEQ ID No:1) or its complementary strand; and
   b) any sequence hybridizing with the sequence a) under strict conditions.

3. The isolated nucleic acid sequence according to claim 1 which is selected from the group consisting of:
   a) the nucleotide sequence of 2590 bp (SEQ ID No:2) or its complementary strand; and
   b) any sequence hybridizing with the sequence a) under strict conditions.

4. A plasmid construct comprising a sequence according to claim 1.

5. A plasmid construct formed by incorporating a sequence of claim 1 into plasmid pLDP1 or plasmid pLAB510.

6. A bacterium which contains a sequence according to claim 1.

7. The bacterium according to claim 6 which is a lactic acid bacterium.

8. The lactic acid bacterium according to claim 7 which belongs to the species *Lactococcus lactis*.

9. A method of transferring genetic material to a strain of industrial interest, which comprises transferring the genetic material by conjugation from a bacterium according to claim 6 to said strain of industrial interest.

10. A strain of industrial interest into which genetic material has been transferred by the method of claim 9.

11. The strain of industrial interest according to claim 10 which is *L. lactis* ssp *lactis* or *L. lactis* ssp *cremoris*.

12. A plasmid construct comprising a sequence according to claim 2.

13. A plasmid construct comprising a sequence according to claim 3.

14. A bacterium which contains a sequence according to claim 2.

15. The bacterium according to claim 14 which is a lactic acid bacterium.

16. The lactic acid bacterium according to claim 15 which belongs to the species *Lactococcus lactis*.

17. A bacterium which contains a sequence according to claim 3.

18. The bacterium according to claim 17 which is a lactic acid bacterium.

19. The lactic acid bacterium according to claim 18 which belongs to the species *Lactococcus lactis*.

20. A bacterium which contains a plasmid construct according to claim 4.

21. The bacterium according to claim 20 which is a lactic acid bacterium.

22. The lactic acid bacterium according to claim 21 which belongs to the species *Lactococcus lactis*.

23. A bacterium which contains a plasmid construct according to claim 5.

24. The bacterium according to claim 23 which is a lactic acid bacterium.

25. The lactic acid bacterium according to claim 24 which belongs to the species *Lactococcus lactis*.

26. A bacterium which contains a plasmid construct according to claim 12.

27. The bacterium according to claim 26 which is a lactic acid bacterium.

28. The lactic acid bacterium according to claim 27 which belongs to the species *Lactococcus lactis*.

29. A bacterium which contains a plasmid construct according to claim 13.

30. The bacterium according to claim 29 which is a lactic acid bacterium.

31. The lactic acid bacterium according to claim 30 which belongs to the species *Lactococcus lactis*.

32. A method of transferring genetic material to a strain of industrial interest, which comprises transferring the genetic material by conjugation from a bacterium according to claim 14 to said strain of industrial interest.

33. A strain of industrial interest into which genetic material has been transferred by the method of claim 32.

34. The strain of industrial interest according to claim 33 which is *L. lactis* ssp lactis or *L. lactis* ssp cremoris.

35. A method of transferring genetic material to a strain of industrial interest, which comprises transferring the genetic material by conjugation from a bacterium according to claim 17 to said strain of industrial interest.

36. A strain of industrial interest into which genetic material has been transferred by the method of claim 35.

37. The strain of industrial interest according to claim 36 which is *L. lactis* ssp *lactis* or *L. lactis* ssp *cremoris*.

38. A method of transferring genetic material to a strain of industrial interest, which comprises transferring the genetic material by conjugation from a bacterium according to claim 20 to said strain of industrial interest.

39. A strain of industrial interest into which genetic material has been transferred by the method of claim 38.

40. The strain of industrial interest according to claim 39 which is *L. lactis* ssp *lactis* or *L. lactis* ssp *cremoris*.

41. A method of transferring genetic material to a strain of industrial interest, which comprises transferring the genetic material by conjugation from a bacterium according to claim 26 to said strain of industrial interest.

42. A strain of industrial interest into which genetic material has been transferred by the method of claim 41.

43. The strain of industrial interest according to claim 42 which is *L. lactis* ssp *lactis* or *L. lactis* ssp *cremoris*.

44. A method of transferring genetic material to a strain of industrial interest, which comprises transferring the genetic material by conjugation from a bacterium according to claim 29 to said strain of industrial interest.

45. A strain of industrial interest into which genetic material has been transferred by the method of claim 53.

46. The strain of industrial interest according to claim 45 which is *L. lactis* ssp *lactis* or *L. lactis* ssp *cremoris*.

* * * * *